(12) United States Patent
Goldfarb (10) Patent No.: US 6,436,135 B1
(45) Date of Patent: Aug. 20, 2002

(54) PROSTHETIC VASCULAR GRAFT

(76) Inventor: David Goldfarb, 5706 E. Horseshoe Rd., Paradise Valley, AZ (US) 85253

( * ) Notice: Subject to any disclaimer, the term of this patent is extended or adjusted under 35 U.S.C. 154(b) by 0 days.

(21) Appl. No.: 05/517,415

(22) Filed: Oct. 24, 1974

(51) Int. Cl.$^7$ .................................................. A61F 2/00
(52) U.S. Cl. ...................... 623/1.39; 623/1.1; 623/1.49; 623/23.71
(58) Field of Search ........................ 3/1, 1.4; 128/92 C, 128/334 R, 334 C, DIG. 14; 260/2.5 R, 2.5 M; 264/288, 289; 623/1.1, 1.39, 1.4, 1.49, 23.64, 23.71, 23.76

(56) References Cited

U.S. PATENT DOCUMENTS

| | | |
|---|---|---|
| 2,642,625 A | 6/1953 | Peck |
| 2,782,180 A | 2/1957 | Weidman |
| 3,008,187 A | 11/1961 | Slade |
| 3,027,601 A | 4/1962 | Barry |
| 3,054,761 A | 9/1962 | Moore |
| 3,060,517 A | 10/1962 | Fields |
| 3,094,762 A | 6/1963 | Juckel |
| 3,105,492 A | 10/1963 | Jeckel |
| 3,158,181 A | 11/1964 | Gore |
| 3,196,194 A | 7/1965 | Ely, Jr. et al. |
| 3,208,100 A | 9/1965 | Nash |
| 3,214,503 A | 10/1965 | Markwood |
| 3,217,083 A | 11/1965 | Gore |
| 3,281,511 A | 10/1966 | Goldsmith |
| 3,304,557 A | 2/1967 | Polansky |
| 3,372,082 A | 3/1968 | Yutaka |
| 3,389,201 A | 6/1968 | Alsup et al. |
| 3,390,067 A | 6/1968 | Miller |
| 3,390,221 A | 6/1968 | Kampmann et al. |
| 3,400,719 A | 9/1968 | Buddecke |
| 3,425,418 A | 2/1969 | Chvapil |
| 3,473,087 A | 10/1969 | Slade |
| 3,479,670 A | 11/1969 | Medell |

(List continued on next page.)

FOREIGN PATENT DOCUMENTS

| | | |
|---|---|---|
| BE | 750553-Q | 5/1969 |
| BE | 767423 | 1/1970 |
| BE | 744984 | 7/1970 |
| BE | 757004 | 10/1971 |
| DE | 1 494 939 | 6/1963 |
| DE | 1494 939 | 6/1963 |
| DE | 1504291 | 10/1969 |
| DE | 1959147 | 6/1970 |
| DE | 1925582 | 12/1970 |
| DE | 1936411 | 1/1971 |
| DE | 2021305 | 1/1971 |
| DE | 2028393 | 4/1971 |
| DE | 2057802 | 6/1971 |
| DE | 2057164 | 9/1971 |
| DE | 2205116 | 10/1972 |

(List continued on next page.)

OTHER PUBLICATIONS

"A New Venous Prosthesis" by T. Soyer et al, *Surgery*, vol. 72, No. 6, pp. 864–872, Dec. 1972, 3–1.4.*

"A–VShunts Created In NewWay" by J.G.R. Volder et al, *Transactions Amer. Society For Artificial Internal Organs,* vol. XIX, pp. 38–42, Published Nov. 13, 1973, Disclosed in Boston, Mass. Apr. 8–9, 1973.*

"A New Vascular Prosthesis for A Small Caliber Artery" by H. Matsumoto et al, *Surgery,* vol. 74, No. 4, pp. 519–532. 3–41.*

(List continued on next page.)

Primary Examiner—Michael J. Milano
(74) Attorney, Agent, or Firm—Wolf, Greenfield & Sacks, P.C.

(57) ABSTRACT

A prosthetic vascular graft with walls less than O.8B millimeters in thickness and formed of highly expanded polytetrafluoroethylene with a microscopic superstructure of nodes and interconnecting fibrils, which nodes are substantially uniformly separated by an average distance greater than a typical red cell. The superstructure of the graft controls transmural cellular ingrowth and assures the establishment and maintenance of a thin,viable neointima.

27 Claims, 2 Drawing Sheets

U.S. PATENT DOCUMENTS

| | | |
|---|---|---|
| 3,512,183 A | 5/1970 | Sharp |
| 3,526,906 A | 9/1970 | Laszlo |
| 3,585,647 A | 6/1971 | Gajewski |
| 3,588,920 A | 6/1971 | Wesolowski |
| 3,609,768 A | 10/1971 | Ayres |
| 3,626,947 A | 12/1971 | Sparks |
| 3,637,906 A | 1/1972 | Parathoen |
| 3,652,759 A | 3/1972 | Schlemmer |
| 3,658,976 A | 4/1972 | Slade |
| 3,664,915 A | 5/1972 | Gore |
| 3,679,614 A | 7/1972 | Shah |
| 3,688,317 A | 9/1972 | Kurtz |
| 3,700,380 A | 10/1972 | Kitrilakis |
| 3,767,500 A | 10/1973 | Tally et al. |
| 3,813,461 A | 5/1974 | Murayama |
| 3,833,455 A | 9/1974 | Rosenblatt, Jr. et al. |
| 3,846,353 A | 11/1974 | Grotta |
| 3,890,417 A | 6/1975 | Vallance |
| 3,908,201 A | 9/1975 | Jones |
| 3,914,802 A | 10/1975 | Reick |
| 3,953,566 A | 4/1976 | Gore |
| 3,957,936 A | 5/1976 | Lauchenauer |
| 3,962,153 A | 6/1976 | Gore |
| 3,992,725 A | 11/1976 | Homsy |
| 4,118,532 A | 10/1978 | Homsy |
| 4,127,706 A | 11/1978 | Martin |
| 4,129,470 A | 12/1978 | Homsy |
| 4,194,040 A | 3/1980 | Breton |
| 4,203,938 A | 5/1980 | Burnett |
| 4,209,480 A | 6/1980 | Homsy |

FOREIGN PATENT DOCUMENTS

| | | |
|---|---|---|
| DE | 2130039 | 12/1972 |
| DE | 2 255 743 | 5/1973 |
| DE | 2417901 | 6/1973 |
| DE | 2413221 | 10/1974 |
| FR | 1243053 | 10/1960 |
| FR | 1317801 | 12/1963 |
| FR | 1580077 | 1/1969 |
| FR | 2134331 | 4/1971 |
| FR | 2118623 | 7/1972 |
| GB | 686438 | 1/1953 |
| GB | 887346 | 1/1962 |
| GB | 981849 | 1/1965 |
| GB | 1076438 | 1/1967 |
| GB | 1057077 | 2/1967 |
| GB | 1071506 | 6/1967 |
| GB | 1120871 | 7/1968 |
| GB | 1174313 | 5/1969 |
| GB | 1161858 | 8/1969 |
| GB | 1169601 | 11/1969 |
| GB | 1240883 | 6/1971 |
| GB | 1284321 | 8/1972 |
| GB | 1 355373 | 6/1974 |
| GB | 1357829 | 6/1974 |
| GB | 1390445 | 4/1975 |
| GB | 1415686 | 11/1975 |
| GB | 1440651 | 6/1976 |
| GB | 1475316 | 6/1977 |
| GB | 1594493 | 7/1981 |
| JP | 7008 165 R | 10/1965 |
| JP | 41-8585 | 5/1966 |
| JP | 67003689 | 2/1967 |
| JP | 67003691 | 2/1967 |
| JP | 13560/67 | 8/1967 |
| JP | 67013560 | 8/1967 |
| JP | 67023980 | 11/1967 |
| JP | 68005554 | 2/1968 |
| JP | 68015644 | 7/1968 |
| JP | 68026359 | 11/1968 |
| JP | 68030016 | 12/1968 |
| JP | 69 00455 | 1/1969 |
| JP | 69007396 | 4/1969 |
| JP | 69007754 | 4/1969 |
| JP | 69022219 | 9/1969 |
| JP | 69022771 | 9/1969 |
| JP | 44-30807 | 12/1969 |
| JP | 69030807 | 12/1969 |
| JP | 70003300 | 2/1970 |
| JP | 70 08 165 | 3/1970 |
| JP | 70008727 | 3/1970 |
| JP | 70008728 | 3/1970 |
| JP | 70019470 | 7/1970 |
| JP | 70030049 | 9/1970 |
| JP | 70036015 | 11/1970 |
| JP | 71011458 | 3/1971 |
| JP | 49042773 | 8/1972 |
| JP | 72040091 | 10/1972 |
| JP | 72040572 | 10/1972 |
| JP | 72050662 | 12/1972 |
| JP | 7300532 | 1/1973 |
| JP | 48-34388 | 5/1973 |
| JP | 48052863 | 7/1973 |
| JP | 42-3691 | 10/1973 |
| JP | 42-23980 | 10/1973 |
| JP | 7334388 | 10/1973 |
| JP | 7334389 | 10/1973 |
| JP | 49005151 | 1/1974 |
| JP | 22792/74 | 2/1974 |
| JP | 49060360 | 6/1974 |
| JP | 49117568 | 11/1974 |
| JP | 49118772 | 11/1974 |
| JP | 49119874 | 11/1974 |
| JP | 50021075 | 3/1975 |
| JP | 41-8585 | 4/1992 |
| NL | 6606343 | 11/1966 |
| NL | 6917 801-Q | 11/1968 |
| NL | 6814336 | 4/1969 |
| NL | 7208704 | 12/1972 |
| RU | 158988 | 1/1963 |
| SU | 240997 | 4/1969 |
| SU | 240996 | 6/1969 |
| SU | 308113 | 9/1971 |

OTHER PUBLICATIONS

"The Use of Plastic Fabrics As Arterial Prostheses" by E.J. Potehtal, *Annals of Surgery,* Oct. 1955, vol. 142, No. 4, pp. 624–632 3–1.*

English Translation of Japanese Patent No. 42–13560, issued August 1, 1967, entitled "A Process for Fabricating Porous Polytetrafluoroethylene".

Dale et al., "Modified Bovine Heterographs for Arterial Replacement," *Annals of Surgery,* vol. 169, No. 6, pp. 927–946 (Jun. 1969).

Campbell et al., Expanded Polytetrafluoro–Ethylene As a Small Artery Substitute, vol. XX *Transactions American Society of Artificial Organs,* pp. 86–90 (1974).

Goldfarb et. al., "Expanded Polytetrafluoroethylene (PTFE): A Superior Biocompatible Material for Vascular Prostheses," vol. XX, *Transactions American Society of Artificial Internal Organs,* (1974).

Matsumoto et al., "A New Vascular Prosthesis for Small Caliber Artery," *Surgery,* vol. 74, No. 4, pp. 519–523 (Oct. 1973).

Poth et al., "The Use of Plastic Fabrics as Arterial Prosthesis," *Annals of Surgery,* vol. 122, No. 4, pp. 624–632 (Oct. 1955) (Originally presented on Apr. 28, 1955).

Sauvage et al., "An External Velour Surface for Porous Arterial Prostheses," *Surgery*, vol. 70, No. 6, pp. 940–953 (Dec. 1971).

Sauvage, "The Future of Porous–Fabric Arterial Prostheses," *The Annals of Thoracic Surgery*, vol. 19, No. 3, pp. 333–335 (Mar. 1975).

Sharp et al., "Rubber Latex Tubing as a Vascular Prosthesis," *American Journal of Surgery*, vol. 105, pp. 802–811 (Jun. 1963).

Sharp et al., "Promotion of a Viable Intima," *Vascular Surgery*, vol. 3, No. 4, pp. 243–249 (Dec. 1969).

Soyer et al., "A New Venous Prosthesis," *Surgery*, vol. 72, No. 6, pp. 864–872 (Dec. 1972).

Volder et al., "A–V Shunts Created in New Ways," vol. XIX *Transactions American Society of Artificial Organs*, pp. 38–42 (1973).

Wesolowski et al., "Porosity: Primary Determinant of Ultimate Fate of Synthetic Vascular Grafts," *Surgery*, vol. 56, No. 1, pp. 91–96 (Jul. 1961).

Wesolowski et al., "Evaluation of a New Vascular Prosthesis with Optimal Specifications," *Surgery*, vol. 59, No. 1, pp. 40–56 (Jan. 1966).

Andrews et al., "Cold Drawing of High Density Polyethylene," *Journal of Materials Science*, 5 pp. 411–417 (1970).

Berkowitz et al., "Pseudointimal Development of Microporous Polyurethane Lattices," vol. XVIII *Transactions American Society of Artificial Organs*, pp. 25–29 (1972).

Berkowitz et al., "Pseudointimal Development on Microporous Polyurethane Lattices," *Surgery*, vol. 72, No. 6, pp. 888–896 (Dec. 1972).

Braunwald et al., "Relation of Pore Size to Tissue Ingrowth in Prosthetic Heart Valves: An Experimental Study," *Surgery*, vol. 57, No. 5, pp. 741–748 (1965).

Bruck et al., "Macromolecular Aspects of Biocompatible Materials—A Review," *Journal of Biomedical Materials Research*, vol. 6, pp. 173–183 (1972).

Campbell et al., Expanded PTFE (Teflon) as a Small Artery Substitute, *Abstacts of ASAIO*, vol. 3, pp. 12 (1974).

Campbell et al., "A Small Arterial Substitute: Expaned Microporous Polytetrafluoroethylene: Pateny Versus Porosity," *Annals of Surgery*, vol. 182, No. 2, pp. 138–143 (1975).

Clark et al., "New Principles Governing the Tissue Reactivity of Prosthetic Materials," *Journals of Scientific Research*, vol. 16, pp. 510–522 (1974).

Calnan, "The Use of Inert Plastic Material in Reconstructive Surgery," *British Journal of Plastic Surgery*, vol. XVI, pp. 1–22, (1963).

Davila et al., "Reprocessed Biological Materials and Mechanical Behavior," Materials in Biomedical Engineering, *Annals of the New York Academy of Sciences*, vol. 146, Art. 1, pp. 138–147 (1968).

Fujiwara et al., "Use of Gortex grafts for replacement of the superior and inferior venae cavae," *The Journal of Thoracic and Cardiovascular Surgery*, vol. 67, No. 5, pp. 774–779 (May, 1974).

Goldfarb et al., "Expanded Polyetrafluoroethylene (PTFE)—A Superior Biocompatible Material for Vascular Prostheses," *Proceedings of the San Diego Biomedical Symposium*, (Feb. 1975).

Gott et al., "Techniques of Applying a Graphite–Benzalkonium–Heparin Coating to Various Plastics and Metals," Vol. X, *Transactions American Society of Artificial Internal Organs*, pp. 213–217 (1964).

Gott et al., "The Coating of Intravascular Plastic Prostheses with Colloidal Graphite," *Surgery*, vol. 50, No. 2, pp. 382–389 (Aug. 1961).

Hamner et al., "Implantable Ceramic Teeth," *Journal of Biomedical Materials Research Symposium*, No. 4, pp. 217–234 (1973).

Hamner et al., "Ceramic Root Implantation in Baboons," *Journal of Biomedical Materials Research Symposium*, No. 3, pp. 1–13 (1972).

Hirschhorn, et al., "Porous Titanium Surgical Implant Materials," *Journal of Biomedical Materials Research Symposium*, No. 2 (Part 1), pp. 49–67 (1971).

Hulbert et al., "Attachment of Prostheses to the Musculo–Skeletal System by Tissue Ingrowth and Mechanical Interlocking," *Journal of Biomedical Materials Research Symposium* No. 4, pp. 1–23 (1973).

Hulbert et al., "Tissue Reaction to Three Ceramics of Porous and Non–Porous Structures," *Journal of Biomedical Material Research*, vol. 6, pp. 347–374 (1972).

Kelly et al., "Development of New Vascular Prosthetic," *Archives of Surgery*, vol. 117, pp. 1367–1370 (Oct. 1982).

Klawitter et al., "Application of Porous Ceramics for the Attachment of Load Bearing Internal Orthopedic Applications," *Journal of Biomedical Material Research Symposium*, No. 4 (Part 1), pp. 161–229 (1971).

Levine, "Survey of Materials for Hard–Tissue Prosthesis," *Journal of Biomedical Material Research Symposium*, No. 2 (Part 1), pp. 5–16 (1971).

Lontz et al., "Extrusion Properties of Lubricated Resin from Coagulated Dispersion," *Industrial and Engineering Chemistry*, vol. 44, No. 8, pp. 1805–1810 (1952).

Matsumoto, "The Need and Current Situation of Anti–thrombotic Substances in the Modern Medical Treatment," *II Symposium on the Medical Applications of High Molecular Compounds: Summaries of Speeches on High Molecular Materials as Anti–Clotting Substances*, pp. 1–15, Feb. 17, 1973.

Matsumoto et al., "Application of Expanded Polytetrafluoroethylene to Vascular Prosthesis, The Fourth Report: Comparison between Expanded Polytetrafluoroethylene and Polytetrafluoroethylene–methylmetacrylate Graftcopolymer Implanted in the Portal Vein," *Artificial Organs*, vol. 3, Supplement, pp. 202–203 (Sep. 30, 1974).

Matsumoto et al., "The Artifical Blood Vessel: the Second Report on the Application of Expanded Polytetrafluoroethylene (former Porous Polytetrafluoroethylene) as the Artificial Blood Vessel, Its Nature and Application to the Vein," *Unknown Source*, pp. 16–17.

Matsumoto et al., "The Application of Expanded Polytetrafluoroethylene to the Trachea" *Unknown Source*, p. 156.

Matsumoto et al., "Studies of Porous Polytetrafluoroethylene as a Vascular Prosthesis: Application to Peripheral Arteries," *Artificial Organs*, vol. 1, No. 1, pp. 44–47 (1972).

Matsumoto et al., "Experimental Studies on Expanded Polytetrafluoroethylene (formerly Called Porous Polytetrafluoroethylene) as Vascular Prosthesis—the Second Report: Its Physiocochemical Properties and Applicability to Veins", *Proceedings of the 10th Japan Congress of Artificial Organs, Artificial Organs*, vol. 1 Supplement, pp. 16–17 (1972).

Matsumoto et al., "Studies on Expanded Polytetrafluoroethylene as the Vascular Prosthesis (the Third Report) Its Antithrombogeneicity, Surface Properties and Porosity," *Artificial Organs*, vol. 3, No. 5, pp. 337–341 (1974).

Matsumoto et al., "Studies on the Porous Polytetrafluoroethylene as a Vascular Prosthesis," *Artificial Organs*, vol. 1, No. 1, pp. 44–47 (1972).

Matsumoto et al., *Translation* of "Application of Expanded Polytetrafluoroethylene as a Vascular Prosthesis—Report No. 3: Anti–Thrombocity in Venous System, Porosity, and Surface Properties," *Artificial Organs*, vol. 3, No. 5 (1974).

Matsumoto et al., "Experimental Studies of Expanded Polytetrafluoroethylene as Vascular Prosthesis—the Second Report: its Applicability to Veins," *Artificial Organs*, vol. 2 No. 5, pp. 262–269 (1973).

Matsumoto et al., *Translation of* "Application of Expanded Polytetrafluoroethylene to Biological Texture," (Source and Date Unknown).

Matsumoto et al., *Translation of* "Studies of Expanded Polytetrafluoroethylene as Vascular Prosthesis (Third Report): Antitrhombogenecity, Surface Properties and Porosity," *Artificial Organs*, vol. 2, Supplement (Proceedings of the 11$^{th}$ General Meeting) (1973).

Motels et al., "Orientation Stretching as a Factor in the Tenacity of Polifen Fibre," *Translation from khimicheskie Volokan*, No. 1, pp. 53–56, (Jan.–Feb. 1971) (As Submitted Herein—pp. 73–77 from 1972 Consultants Bureau).

Motels et al., "The Effect of Stretching on the Faults in Polifen Fibre," *Translation from Khimiches–kie Volokna*, No. 2, pp. 74–75 (Mar.–Apr. 1971) (As Submitted Herin—pp. 220–221 from 1972 Consultants Bureau).

Moynihan, "The Molecular Structure of Perfluorocarbon Polymers. Infrared Studies on Pelytetrafluoroethylene," Unknown Source, (Jan. 13, 1958).

Najjar et al., "The use of small–diameter Dacron grafts with wall–bonded heparin for venous and arterial replacement: Canine studies and preliminary clinical experience," *Surgery*, vol. 68, No. 6, pp. 1053–1063 (1970).

Norton et al., Replacement of Portal Vein During Pancreatectomy for Carcinoma, *Surgery*, vol. 77, No. 2, pp. 280–284 (1975).

Nuwayser et al., "Research Materials Compatible with Blood," *Proceedings of Artificial Heart Program Conference*, pp. 153–168 (1969).

Parsonnet et al., "Autogenous polypropylene–supported collagen tubes for long–term arterial replacement," *Surgery*, vol. 70, No. 6, pp. 935–939 (1971).

Perepelkin, "Theoretical and Maximum Attainable Strength of Various Uniaxially Oriented Polymers (Film. Fibers)," *Mekhanika Polimerov*, vol. 2, No. 6, pp. 845–856 (1966).

Ribbans, "Unsintered Tape Manufacture of Calendering Round Rods," *Report of E.I. Dupont De Nemours & Co, Technical Services Laboratory, Plastics Department*, (Mar. 15, 1966).

Salvatore et al., "An Experimental Study of the Influence of Pore Size of Implanted Polyurethane Sponges Upon Subsequent Tissue Formation," *Surgery*, vol. 112, pp. 463–468 (Jan. to Jun. 1961).

Sauer et al., "The Role of Porous Polymeric Materials in Prosthesis Attachment," *J. Biomed. Mater. Res. Symposium*, No. 5 (Part 1), pp. 145–153 (1974).

Taylor et al., Porous Methyl Methacrylate as an Implant Material, *J. Biomed. Mater. Res. Symposium*, No. 2 (Part 2), pp. 467–479 (1972).

Thompson, Jr. et al., "Paste Extrusion," *Modern Plastics*, pp. 115–122 (Feb. 1956).

Tynnyi et al, "Effect of Strain Rate on the Strength of Polymer Materials in Liquid Media," *Soviet Materials Science*, pp. 566–568 (1969).

Volder et al., "Induced Growth of Connective tissue in Cardiovascular Prosthesis," Vol. XX, *Transactions of American Society of Artificial Internal Organs*, pp. 521–529 (1974).

Wesolowski et al., "Artificial Arteries," *AORN Journal*, pp. 35–50 (Jan. 1968).

Wesolowski et al., "Considerations in the Development of Small Artery Prostheses," vol. XIV, *Transactions of American Society of Artificial Internal Organs*, vol. XIV, pp. 43–47 (circa 1970).

Wesolowski et al., "The compound Prosthetic Vascular Graft: A Pathologic Survey," *Surgery*, vol. 53, No. 1, pp. 19–44 (1963).

Wesolowski, "Some Problems Concerning the Assessment of Arterial Prosthetic Materials," *J. Biomed. Mater. Res.*, vol. 1, pp. 171–174 (1967).

Whiffen et al., "Heparin Application to Graphite–coated Intravascular Prostheses," *Surgery*, vol. 36, No. 2, pp. 404–412 (Aug. 1964).

White et al., "Preliminary Report: Evaluation of Tissue Ingrowth into Experimental Replamineform Vascular Prostheses," *Surgery*, vol. 79, No. 2, pp. 229–232 (1976).

Winter, "Transcutaneous Implants: Reactions of the Skin–Implant Interface," *J. Biomed. Mater. Res. Symposium*, No. 5 (Part II), pp. 99–113 (1974).

Yamaguchi et al., "Effect of Stretching upon the structure of the Properties of Polytetrafluoroethylene Plate," *Research Reports of the Kogakuin University*, No. 24, pp. 60–70 (1968).

Yamaguchi et al., *Translation of,* "Effect of Stretching upon the Structure of the Properties of Ethylene Tetra–fluoride Resin," *Research Reports fo the Kogakuin University*, No. 24, pp. 1–19 (May 1968).

Dupont Article re: 62TFE–fluorocarbon resin, (pre 1974?).

Dupont Article re: 6A TFE–fluorocarbon resin, (pre 1974?).

Dupont Article re: 64TFE–fluorocarbon resin, (pre 1974?).

Dupont Article re: 6C TFE–fluorocarbon resin, (pre 1974?).

Dupont Information Bulletin re: Teflon 6 and 6C (pre 1974?).

Tetrafluoroethylene Polymers, *Encyclopedia of Polymer Science and Technology*, vol. 13, pp. 642–644 (pre 1974?).

"Fluorocarbon Polymers," *Properties of Commercial Polymers*, pp. 419–429 (pre 1974?).

Matsumoto et al., *Translation of,* "Experimental Studies on Synthetic Prosthesis for the Portal Vein," presented at the 75$^{th}$ meeting of the Society of Surgery, Apr. 3, 1975.

Matsumoto et al., *Translation of,* "The Prerequisites for Venous Implanting," presented at the 75$^{th}$ Japanese Society of Surgery, Apr. 4, 1975.

Matsumoto et al., *Translation of,* "Application of Expanded Polytetrafluoroethylene as Vascular Prosthesis—Report#3 : Anti–Thrombogenecity in Venous System, Porosity, and Surface Properties," *Artificial Organs*, vol. 3, No. 5 (1974).

Matsumoto et al., *Translation of,* "Application of Expanded Polytetrafluoroethylene to Biological Structure," (Date and Publication unknown).

Matsumoto et al., *Translation of,* "Application of Expanded Polytetrafluoroethylene to Artificial Blood Vessels (4$^{th}$ Report on the Comparison with Polytetrafluoroethylene–Methyl–methacrylate Graft Copolymer in the Portal Vein System," (Date and Publication unknown).

Matsumoto et al., "A New Vascular Prosthesis for a Small Caliber Artery," (pre 1974?).

Bassett et al, "On Crystallization Phenomena in Polytetrafluoroethylene," *Polymer*, vol. 15, (1974).

English translation of Japanese publication JP 41–8585 (1966).

English translation of German publication DE 1,494,939 (1963).

Information Bulletin, "TFE–Fluorocarbon Resins Molding Techniques," (Pre 1973?).

Lewis et al., "Rheology of Lubricated Polytetrafluoroethylene Compositions," Reprinted from *Industrial and Engineering Chemistry*, vol. 45, pp. 1123–1127 (1953).

Price List for USCI, 1972.

Ribans, "High Quality Hose Constructions From Teflon TFE Fluorocarbon Resins," (1965).

Speerschneider et al., "Some Observations on the Structure of Polytetrafluoroethylene," *Journal of Applied Physics*, vol. 33 No. 5, pp. 1871–1874 (1962).

Suwa et al., "Melting and Crystallization Behavior of Poly(tetrafluoroethylene). New Method for Molecular Weight Measurement of Poly(tetrafluoroethylene) Using a Differential Scanning Calorimeter," *Journal of Applied Polymer Science*, vol. 17, pp. 3253–3257 (1973).

* cited by examiner fig. 1 fig. 2 fig. 3

PROSTHETIC VASCULAR GRAFT

The present invention relates to prosthetic vascular structures and, more particularly, to vascular prostheses fabricated from highly expanded polytetrafluoroethylene.

Frequently in cardiovascular surgery, it is necessary to bypass or replace blood vessels, whether veins or arteries, to assure an adequate and balanced blood flow to particular organs, extremities or areas of the body.

Unsuccessful attempts were made during the early years of this century to implant prosthetic or artificial vessels fabricated from glass and metal. With the availability of inert synthetic materials such as nylon, Orlon, Dacron and Teflon (polytetrafluoroethylene or PTFE) during the late 1940's and early 1950's, large arterial replacements were achieved with increasing degrees of success.

Cardiovascular surgeons presently have available knitted and woven vessels of Dacron and Teflon which may be used as replacements for arteries having relatively large inside diameters (approximately 7 millimeters). However, no clinically acceptable small arterial prosthesis has been available; and surgeons have found it necessary to scavenge marginally important or superficial vessels, such as the saphenous vein, to serve as replacements for defective small bore arteries.

It is a principal objective of the present invention to provide a prosthetic vascular structure capable of replacing or bypassing natural blood vessels having relatively small inside diameters as well as those vessels of intermediate and large bore.

The transplantation of saphenous veins from the patient's legs to more critical portions of the cardiovascular system entails numerous disadvantages: The entire surgical procedure is unduly protracted by having to first excise the venous replacement from one part of the patient's body, then prepare the replacement for implantation, and finally implant the substitute vessel at another point in the patient's cardiovascular system. Prolonged exposure to anesthesia and multiple incisions combine to increase the probability of both infection and post-operative discomfort.

Cardiovascular surgery frequently requires grafts of various lengths and diameters in achieving, for example: the femoral artery to popliteal artery bypass, the coronary artery bypass, the renal artery bypass, etc.. Occasionally, however, especially in older patients, the saphenous veins themselves are inadequate for use as replacements; and in some instances only unacceptably short segments of the saphenous veins are available for transplantation.

It is another object of the present invention to provide an artificial vascular structure which may be prefabricated in various lengths and diameters, thereby eliminating unnecessary incisions, minimizing exposure to anesthesia, conserving already limited surgical resources, and assuring an ample supply of small bore vascular replacements.

Operations such as the femoral/popliteal bypass require especially long grafts which ideally taper in cross-sectional area from their proximal to their distal ends. Heretofore, transplanted saphenous veins have been used to accomplish this bypass procedure. Because blood flow through the saphenous vein is unidirectional in character, it is necessary to reverse the vein when it is being used as an arterial substitute. The inside diameter of a saphenous vein naturally tapers between its proximal and distal ends. Reversing the vein for implantation between the femoral and popliteal arteries results in a corresponding reversal of this taper so that the smaller diameter end must be grafted to the relatively large femoral artery while the larger diameter end is grafted to the relatively small popliteal artery. The reversed taper of an implanted saphenous vein causes deceleration of the blood flow while the turbulence inducing discontinuities at the bypass junctures contribute to stasis and associated thrombosis.

It is a further object of the present invention to provide a small bore prosthetic vascular structure which may be fabricated in relatively long segments, which segments decrease in inside diameter between proximal and distal ends so as to facilitate their implantation as peripheral artery replacements and assure a close hemodynamic simulation of the corresponding natural vessel.

The inner surface of natural blood vessels is characterized by a thin, delicate layer of endothelial cells known as the intima. The primary function of this layer is to provide a smooth interface between the blood stream and the vessel wall. For example, a ruptured artery may, after healing, include rough or irregular protrusions from the wall into the blood stream. As the natural intima reestablishes itself over the wound area, it serves to lessen the severity Ln irregular wall transitions and thereby assure laminar blood flow.

While the outer surface of a vessel prosthesis is encapsulated by fibrous growth as a result of normal rejection processes, the inner surface typically becomes isolated from the blood stream by a layer which has been referred to, with varying degrees of accuracy, as the neointima or pseudointima. To be classified as a true neointima, it would be necessary for the inner surface of the artificial vessel to be covered with an extremely thin lining of viable endothelial cells. Although such a lining would vary in thickness from point to point, it would be typically less than ten cells thick. There has heretofore existed no known vessel prosthesis of any size or configuration which, when implanted, would support the growth and maintenance of a true neointima layer. Accordingly, the vessel/blood interface associated with state of the art prostheses is characterized by a pseudointima consisting at best of a few irregularly distributed islands of endothelial growth but made up largely of compacted fibrin which has been flow sculptured by the blood stream. Occasionally, portions of this pseudointima will fracture or particulate and introduce emboli into the patient's blood stream.

The formation and maintenance of a true neointima requires a continuous extravascular source of nourishment to supplement whatever nourishment might be supplied by diffusion from the adjacent blood stream. In extremely short grafts (less than 2 to 3 centimeters), cellular ingrowth has been observed along the inside surfaces from the suture lines at the ends of the graft. In such cases, the tissue growth, augmented by capillary ingrowth, can provide a continuous nutrition route capable of supporting a viable neointima. However, the thickness of this inner layer of tissue is so great as to virtually occlude all but large bore grafts. Not only is ingrowth of this type unpredictable but it can be expected or tolerated at all only in very short grafts of relatively large inside diameter.

Extensive efforts have been made toward the fabrication of a porous vascular structure which would permit uniform transmural tissue ingrowth sufficient to assure the formation and continuous nutrition of a true neointima layer. The culmination of this prior art effort is represented by grafts which are machine woven from threads consisting of tightly twisted Dacron or Teflon fibers. The threads used in the manufacture of these woven grafts, while extremely small by garment industry standards, are enormous when viewed in the context of a hemodynamic system under pressure. As is true of any knitted or women fabric, the minimum size of the interstices between threads is determined by the diameter of the threads themselves. Because these interstices or voids are quite large in woven grafts, it is necessary to preclot the graft by dipping it in blood in order to prevent excessive transmural leakage after implantation.

The large size of the threads used in prior art woven grafts and the tightness with which the constituent fibers are twisted renders each individual thread virtually impenetrable to cellular ingrowth and virtually beyond cellular circummigration. From the viewpoint of a single fibroblast, a knitted vessel prosthesis looks like two or three mammoth structures separated by equally mammoth voids which have been filled by the clotting process with masses of coagulated fibrin and proteinaceous matter. Viewed on a similar microscopic basis, the inner wall of the knitted graft appears as a series of large, rough cylinders of inert material separated by cavities which are equal or larger in breadth and depth to the diameter of the cylinders. As the blood flows through a prosthetic vessel of this type, the cavities are filled with slow moving blood while the irregularity and protrusion of the threads promotes turbulent blood flow. Thrombosis throughout the wall of the graft and at its inner surface, combined with the large size and separation of the knitted threads, serves to initiate buildup of an irregular pseudointima layer while at the same time blocking and inhibiting transmural cellular ingrowth of the type necessary for the support of a uniform, viable neointima.

Accordingly, it is a major objective of the present invention to provide a homogeneously porous vascular prosthesis characterized by small nodes interconnected by extremely fine fibrils to form an open superstructure which will allow uniform, controlled transmural cellular ingrowth and thereby assure the establishment and maintenance of a thin, viable neointima as well as firm structural integration of the graft into the body.

It is another objective of the present invention to provide a porous vascular prosthesis characterized by a superstructure which is substantially impermeable to the flow of relatively high viscosity liquids such as blood at normal pressures.

Briefly stated, the invention constitutes a prosthetic vascular device formed from a small bore tube of polytetrafluoroethylene which has been heated, expanded and sintered so as to have a microscopic superstructure of uniformly distributed nodes interconnected by fibrils and characterized by: (a) an average internodular distance which is (i) large enough to allow transmural migration of typical red cells and fibroblast, and (ii) small enough to inhibit both transmural blood flow at normal pressures and excessive tissue ingrowth; and (b) an average wall thickness which is (i) small enough to provide proper mechanical conformity to adjacent cardiovascular structures, and (ii) large enough, when taken in conjunction with the associated internodular distance, to prevent leakage and excess tissue ingrowth, to allow free and uniform transmilral nutrient flow, and to assure mechanical strength and ease of implantation.

The invention is pointed out with particularity in the appended claims; however, other objectives and advantages, together with methods for making and using the invention, will be better understood by referring to the following detailed description taken in conjunction with the following illustrations wherein:

Figure 1:
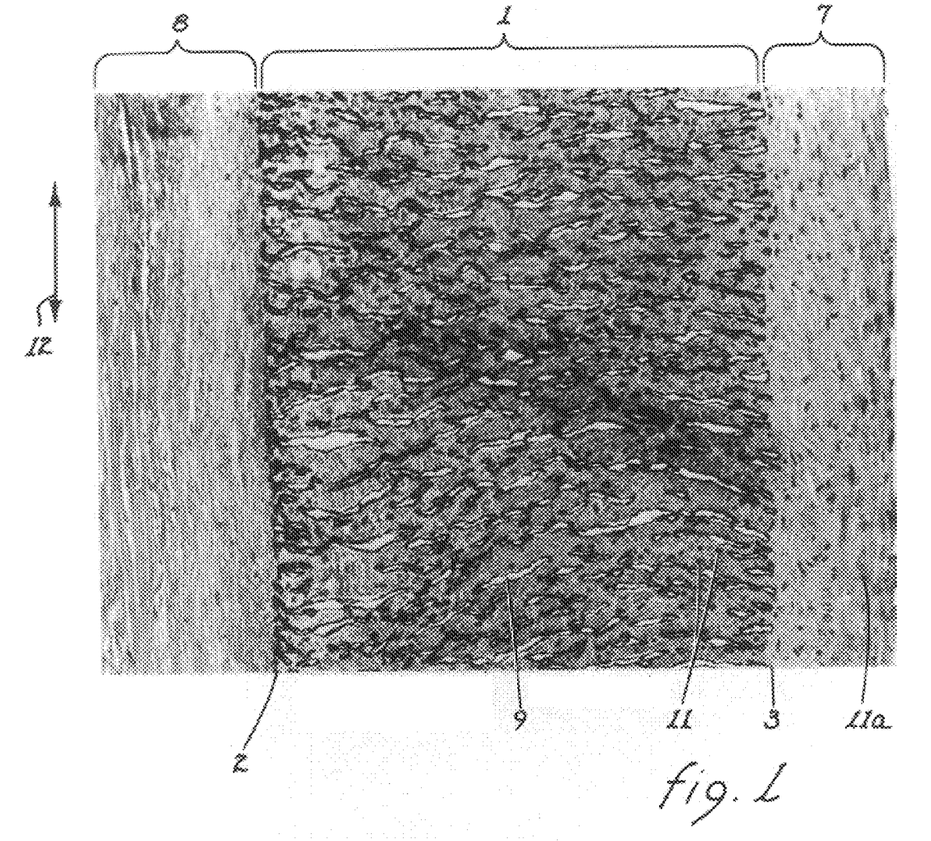
FIG. 1 is a photomicrograph, taken at 250X, of a section through the wall of a vascular graft embodying the present invention after having been implanted as a femoral artery segment for a period of eight months.

Referring to FIG. 1, it is seen that the graft of the present invention consists of a wall 1 having an outer surface 2 and an inner surface 3. Corresponding numerical denominations have been applied to the macroscopic view of the graft shown in FIG. 3 where the cutaway section shows the plane of wall 1 depicted in the photomicrograph of FIG. 1.

Figure 3:
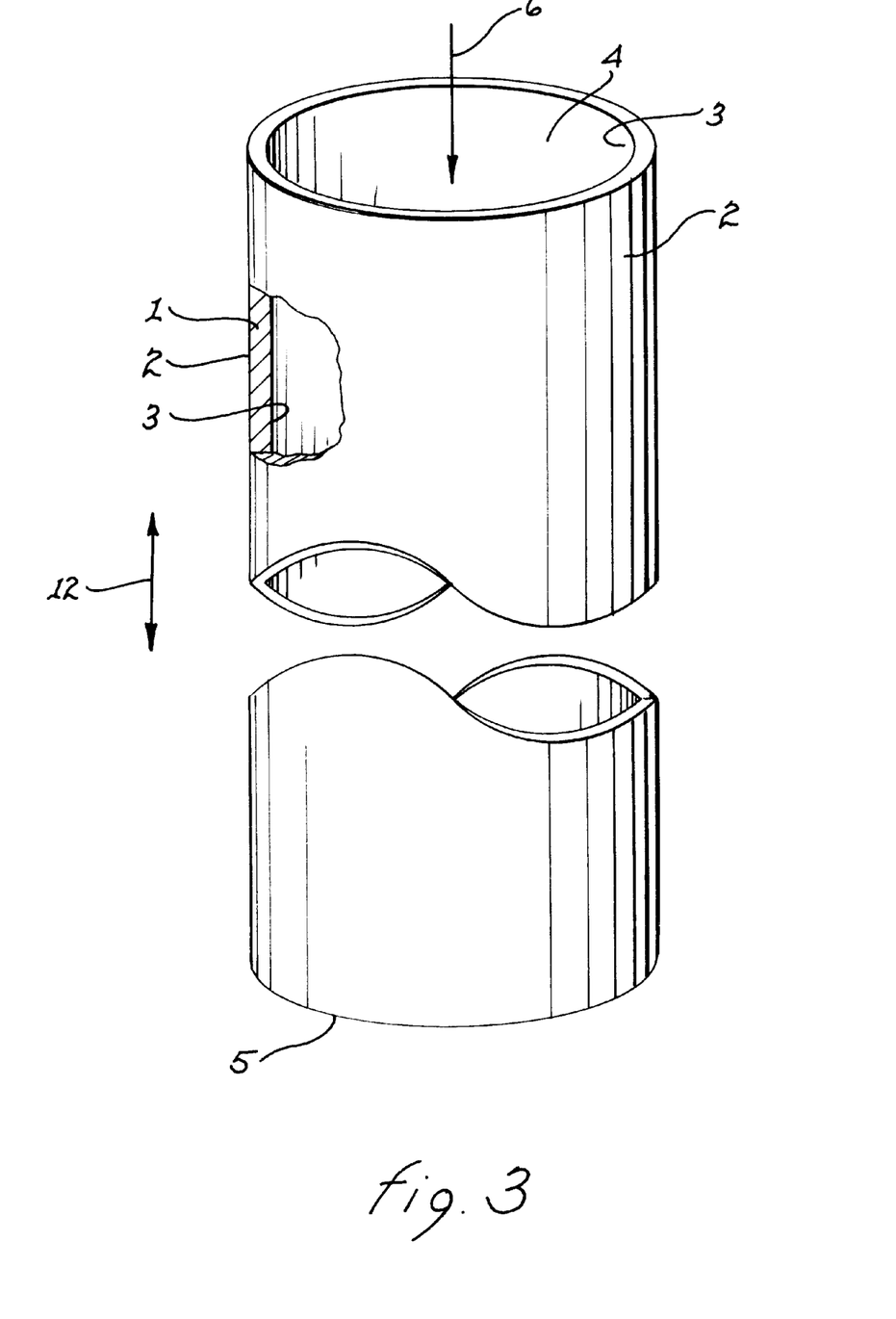
FIG. 3 is a macroscopic stylization of a graft segment showing the sectional plane viewed in FIG. 1.

The graft as shown generally in FIG. 3 is further characterized by a proximal end 4 and a distal end 5. By convention, blood flow through the graft is in the direction indicated by arrow 6, i.e., from the proximal end 4 to the distal end 5.

As can be seen in FIG. 1, the inner surface 3 of graft wall 1 is covered by a uniform layer of endothelial cells forming the neointima 7. The outer surface 2 is covered by a uniform, firmly attached, encapsulation 8 of collagenous matter which includes substantial capillary ingrowth (not shown).

The graft wall 1 is a superstructure made up of polytetrafluoroethylene nodes 9 which appear in FIG. 1 as irregularly shaped islands of inert white material. The polytetrafluoroethylene nodes 9 are interconnected by fine fibrils which, because of their extremely small diameters and their disaffinity for photographic stain, are not visible in FIG. 1.

Figure 2:
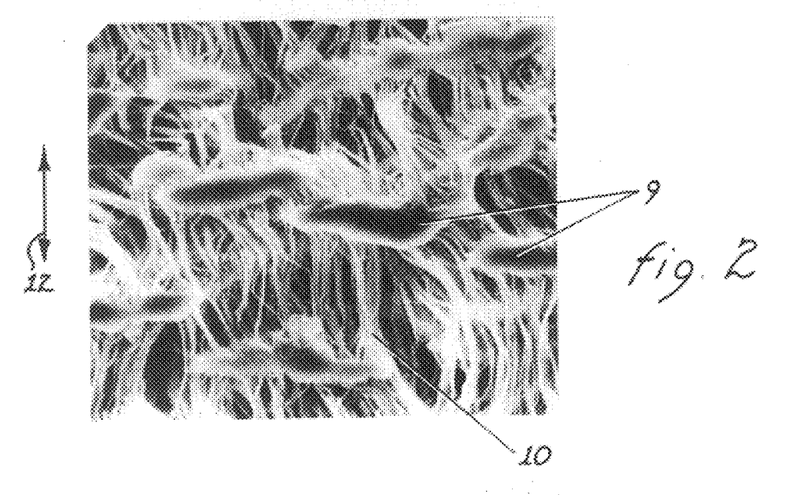
FIG. 2 is a photomicrograph, taken by means of a scanning electron microscope at 1000X, showing the node and fibril superstructure characterizing highly expanded polytetrafluoroethylene vessel prostheses embodying the present invention.

FIG. 2 depicts the node/fibril superstructure of FIG. 1 prior to implantation. The polytetrafluoroethylene nodes 9 and the many interconnecting fibrils 10 may be clearly observed in the absence of cellular ingrowth and at a magnification of approximately 4 times greater than FIG. 1. On the other hand, the implanted graft of FIG. 1 has been thoroughly and uniformly permeated by fibroblasts having cellular nuclei which appear in the photomicrograph as black dots 11. The nuclei of the endothelial cells forming the neointima 5 appear as black dots lla in FIG. 1. As may be observed, the neointima is approximately eight cells in thickness.

Methods and techniques for expanding polytetrafluoroethylene have been known for many years. One of the earliest disclosures containing a discussion of such methods and resultant products is found in Japanese Patent No. 13,560/67 which was filed Nov. 1, 1963 and officially published on Aug. 1, 1967. Partially expanded polytetrafluoroethylene has been used to provide electrical insulation on cables and to form low friction structural members such as bearings and piston rings, to provide sealing in liquid systems, and, without clinically meaningful or reproducible success, for artificial vessel replacements. See for example, Japanese Patent No. 13,560/67; Soyer, et al, "A New Venous-Prosthesis", Surgery, Vol. 72, page 864 (December 1972); and Matsumoto, et al, "A New Vascular Prosthesis for Small Caliber Artery", Surgery, Vol. 74, page 519 (October 1973).

The basic process for expanding polytetrafluoroethylene is quite simple: The constituent resin is first subjected to shear by, for example, extrusion into the desired geometrical configuration. The extrudate is then heated at a temperature below the sintering temperature of 327° C. and physically stretched or expanded along at least one axis. The expanded member is then physically restrained against contraction and is sintered by brief exposure to temperatures in excess of 327° C. , thereby crystallizing the expanded structure and providing moderate tensile strength of up to approximately 6500 psi. As the raw extrudate is stretched, the non-porous polytetrafluoroethylene separates into solid nodes 9 of polytetrafluoroethylene which remain structurally interconnected by polytetrafluoroethylene fibrils 10 which are drawn from the nodes during expansion. See FIG. 2. Node size and distribution in the final product is adversely affected by: very rapid expansion, uneven expansion, insufficient heating, non-uniform heating, and irregularly distributed expansion forces. The distance between nodes 9 is directly proportional to the extent to which the extrudate has been expanded. When polytetrafluoroethylene is properly expanded along one axis, virtually no dimensional changes are observed in the orthogonal direction. The directional vector 12 in FIGS. 1, 2 and 3, indicates the axis along which grafts embodying the present invention are typically expanded.

As can be seen in FIGS. 1 and 2, the nodes 9 are crudely ellipsoidal in configuration with their major axis disposed at approximately right angles to the axis of expansion 12. The nodes 9 are of random but generally uniform size and are distributed in a homogeneous pattern throughout the wall 1. Furthermore, the nodes are extremely small, typically less than a few times the size of a normal fibroblast or red cell.

Because the minor axes of the ellipsoidal nodes 9 are transverse to the generally radial direction typifying cellular ingrowth, the invading fibroblasts never encounter any massive polytetrafluoroethylene barrier. It is believed that the size and orientation of the nodes 9, together with their tapered configuration, facilitates cellular migration and ingrowth. To avoid substantial impediment to ingrowth, the average minor axis dimension of the nodes 9 is less than three times the major dimension of a typical red cell, i.e., less than about 18 microns.

It has been found that the average internodular distance, as measured along the axis of expansion 12, must fall within a relatively narrow range of values, viz., between approximately 6 and 80 microns. As will be appreciated by those skilled in the art, the term "average" when used in conjunction with internodular distance and node size cannot be used or interpreted with statistical precision; rather, the term is intended to connote a nominal or typical dimension derived from a broad sample. By way of example, where the average internodular distance is said to be 30 microns, it would be expected that some of the nodes would be separated by only a few microns while others might be separated by 90 or 100 microns. In the ideal graft, each node 9 would have a perfect elongated football shape and would be separated from its neighbors by uniformly distributed fibrils 10 of equal lengths. Unfortunately, such perfection is rarely, if ever, achieved in a microscopic environment.

Where the average internodular distance is less than the major dimension of a typical red cell, or approximately 6 microns, inadequate cellular ingrowth has been observed. In such cases, the node/fibril superstructure is so tightly packed as to preclude either the establishment or continued nutrition of a viable neointima.

Associated with (very large internodular distances is a loss of tensile strength and overall structural integrity. The graft becomes progressively more pliable and progressively more difficult to handle during surgery. Excessively expanded grafts will be subject to deformation and leakage at the suture line. Furthermore, excessive cellular ingrowth has been observed in grafts having an average internodular in excess of approximately 80 microns. Where the inside diameter of the graft is critically small, excessive cellular penetration of this type can lead to the formation of a pseudointima or an unacceptable thickening of the neointima with an accompanying occlusion of the lumen.

As the average internodular distance is extended beyond, for example, 150 to 200 microns, the graft superstructure becomes progressively more permeable to blood flow and is characterized by substantial interstial clotting and progressively decreasing and non-uniform cellular ingrowth. Ultimately, were it possible to reproduce internodular distances comparable in size to the interstial voids of the size characterizing woven grafts, then virtually all transmural growth would be inhibited, and the support of a true neointima would be impossible.

Just as the nodes 9 must be of such size, configuration and orientation to avoid substantial impediment to cellular ingrowth, so too, they must be substantially uniformly distributed throughout the length and cross-section of the graft. It has been found that clumps or groupings of closely packed nodes can serve as barriers to ingrowth. It has also been found particularly critical to the creation and support of a viable neointima, that the nodes immediately adjacent to and defining the inner surface 3 of the graft be uniformly distributed, i.e., neither clumped so as to block the flow of nutrition to the neointima nor so widely spaced as to define deep thrombosis inducing irregularities in the inner wall 3.

A phenomenon referred to as "skin effect" is attributed to non-uniform force distribution occurring either during the extrusion or the expansion of tubular structures of the type embodying the present invention. Skin effect involves a relatively high concentration of nodes in a given circumferential plane, usually either the inner surface 3 or the outer surface 2. A slight skin effect is observed on the outer surface 2 of the graftssegment shown in FIG. 1, while the inner surface 3 is characterized by an open regular node pattern. The limited skin effect observed at outer surface 2 is obviously acceptable in degree since, as FIG. 1 clearly shows, it has not adversely affected cellular ingrowth.

In some instances, skin effect is a highly localized phenomenon, yet in other instances it may be observed over the entire inner or outer surface of the graft. A skin effect which might be acceptable at the outer surface of the graft might well be unacceptable at the inner surface because of the greater criticality for establishing a regular superstructure which will allow ample and uniform nutrient flow to, and mechanical support for, the neointima 7.

Wall thickness is another factor affecting the establishment and maintenance of a viable neointima in grafts embodying the present invention. For any particular internodular distance within the acceptable range, the thickness of the graft wall can be made so great as to preclude complete transmural cellular migration and ingrowth.

Nutrition of the fibroblasts in wall 1 as well as the endothelial cells forming the neointima 7 depends primarily upon capillary ingrowth, which normally becomes well developed within the third and fourth weeks after implantation of the graft. Diffusion of nutrients from the blood stream itself, especially during the period immediately following implantation, and transmural diffusion of nutrition also contribute to tissue growth.

There is a limit to which cellular ingrowth will penetrate from the outer surface 2 into a graft wall. The depth or extent of nutritional diffusion is also limited. Where the wall of a particular graft is too thick (considering the internodular distance), an unnourished calcifying layer will form within the wall of the graft in any area which is so far removed from the outer surface 2 as to be beyond the range of normal cellular ingrowth and which is too far from the inner surface 3 to receive nutrients by diffusion from the blood stream. This calcifying layer, itself a result of inadequate nutritional flow, acts as a barrier, further inhibiting the growth of new cells. Within the acceptable range of average internodular distances, it has been found that wall thicknesses greater than approximately 0.8 millimeters are excessive.

While excessive wall thickness may result in an unacceptably stiff graft or one which inhibits transmural ingrowth, insufficient wall thickness results in a limp, unmanageable graft or one which allows excessive cellular ingrowth. Thus, wall thickness and internodular distance are the two prime determinants of graft pliability and strength and are also the two major factors which combine to control the extent and uniformity of transmural ingrowth.

Grafts embodying the present invention, having wall thicknesses in the range between 0.2 and 0.8 millimeters and characterized by internodular distances in the range between 6 and 80 microns have exhibited excellent mechanical properties and have resulted in controlled ingrowth sufficient to assure the support of a thin, viable neointima which does not unduly restrict the lumen of the graft. Grafts falling outside these ranges have been found to be marginal or clinically unacceptable. Grafts falling into these preferred ranges are characterized by moderately high tensile strength in the range between 2500 and 6500 pounds per square inch and average density between 0.2 and 0.5 grams per milliliter.

In the introductory portion hereof it was pointed out that reversed saphenous vein grafts have been frequently used to bypass diseased segments of peripheral arteries. This requires anastomosis of the graft to arteries having substantially different diameters. The proximal artery always has a larger diameter than the distal artery, as is true, for example, in the case of the common femoral artery-to-popliteal artery bypasses performed for the purpose of routing blood flow around obstruction in the superficial femoral artery. The femoral artery normally has a diameter of 6 to 8 millimeters whereas the popliteal artery is typically between 3 and 4 millimeters in diameter. If a constant diameter prosthesis or a reversed saphenous vein is used in accomplishing the bypass, a sudden cross-sectional area change is present at either or both ends of the graft. From a hemodynamic point of view, these sudden area changes are highly disadvantageous in that they tend to produce turbulence with pockets of stasis, causing deposition of platelets, fibrin and cellular materials and thus the formation of thrombi which can ultimately propagate to occlusion of the vessel. These problems are eliminated in accord with one embodiment of the present invention wherein the inside diameter of the prosthesis tapers gradually over its entire length from the diameter of the larger proximal vessel down to the diameter of the smaller distal vessel. Tapering of the graft promotes streamlining of the blood and assures laminar rather than turbulent flow. Tapering also results in accelerated blood flow with an associated increase in the velocity of the blood elements; as opposed to deceleration, which characterizes flow through the reversed saphenous vein. Thus, tapered grafts of the present invention not only provide for the growth and maintenance of a viable neointima but also promote accelerated laminar blood flow with the resultant elimination of clotting due to stasis and turbulence.

In addition to the significant biomedical, hemodynamic and mechanical advantages which accompany the use of vessel prostheses of the type described herein, numerous surgical, procedural and post-operative benefits are also realized. Cardiovascular surgery calling for a small bore vessel substitute has heretofore required initial harvesting of the saphenous vein for use as a graft. This involves the following surgical steps which are rendered unnecessary by the present invention:

1. groin incision and proximal dissection of the patient's saphenous vein;
2. lower thigh incision and distal dissection of the patient's saphenous vein;
3. multiple medial thigh incisions for completion of the saphenous vein dissection;
4. removal of the saphenous vein and careful ligation of all branches;
5. reversal of the saphenous vein prior to implantation so that venous valves do not obstruct arterial flow, thereby necessitating the awkward anastomosis of the small (approximately 3 millimeters) distal end of the vein to a substantially larger proximal artery and, in the case of a peripheral artery replacement, anastomosis of the relatively large proximal end of the vein to a very small bore distal artery;
6. careful inspection for possible leaks from the various branches in the graft or from those remaining in the patient's thigh; and,
7. closing of the multiple incisions necessitated by removal of the saphenous vein.

Use of expanded polytetrafluoroethylene grafts of the type described and claimed herein not only eliminates these unnecessary surgical procedures, but also shortens operative and anesthetic time by between one and two hours, does away with the post-operative discomfort and possible infection resulting from numerous leg wounds and greatly conserves already limited hospital and surgical resources.

The manufacture of prosthetic vascular structures embodying the present invention is extremely simple and can be readily performed with the most rudimental laboratory equipment, realizing of course that more sophisticated equipment is required for volume production and quality control. The basic physical, chemical and procedural parameters for expanding polytetrafluoroethylene are presented and discussed in the previously cited Japanese Patent No. 13,560/67; however, an example will be given illustrating the fundamental technique involved in making small bore polytetrafluoroethylene grafts having the claimed structure.

Polytetrafluoroethylene is extruded to form tubing having an average inside diameter of approximately 4 millimeters and an average wall thickness of approximately 0.5 millimeters. Unsintered tubing of this type, identified by the manufacturer's No. S16882-7, may be obtained from W. S. Shamban Company (71 Mitchell Road, Newberry Park, Calif. 91320). The unsintered extrudate, which is quite fragile, is carefully cut with a razor blade into lengths of, for example, 7.3 centimeters. Small aluminum plugs of virtually any configuration are inserted into the end of the tubing and secured thereto by tightly wrapped stainless steel wire. A relatively short end segment is thus confined between the inserted plug and the stainless steel wire. These plugs provide points for handling and attachment during the subsequent heating, elongation and sintering steps.

The tubing and plug assembly is placed in a uniformly heated oven for approximately one hour at 275° C. Thereafter, the assembly is removed from the oven, the plugs are grasped and stretched apart manually to obtain a tubular length of 23 centimeters. The time required for removal and elongation should be made as short as possible to reduce the effects of cooling. Elongation should be carried out at a moderate, uniform rate and the plugs should be moved apart along a common axis of expansion to assure uniform force distribution. Typically, this manual operation has required less than ten seconds and has yielded good results.

The elongated assembly is then secured against contraction by restraining the plugs at the desired separation. This may be achieved in any number of obvious ways, as for example, by using plugs with enlarged ends which are placed in a fixture having U-shaped slots separated by the desired distance of 23 centimeters.

While still restrained, the elongated assembly is returned to the oven for approximately forty-five seconds at 400° C., during which time the node/fibril superstructure is sintered and becomes fixed. The elongated grafts are then cut to the desired lengths and after sterilization are ready for implantation.

In large commercial applications, expansion is achieved mechanically in the oven itself at closely controlled rates and is immediately followed by sintering. However, excellent grafts, such as the one shown in FIG. 1, have been obtained by the simple laboratory techniques outlined above.

Fabrication of tapered grafts such as those used for peripheral artery replacement involves the additional step of reshaping a sintered tube of desired length and diameter over a tapered stainless steel mandrel which has been heated to approximately 300° C. After the entire assembly is allowed to cool, the slightly re-expanded graft retains the shape of the mandrel and may be removed for use without further heat treatment.

It will be apparent to those skilled in the art that the disclosed prosthetic vascular structure may be modified in numerous ways and may assume many embodiments and configurations other than those specifically set forth and described above. For example, the basic prosthetic structure may be made various lengths and in diameters up to approximately 40 millimeters without affecting the structural integrity or operativeness of the graft. Various secondary configurations such as bifurcated grafts may also be produced. Because grafts embodying the present invention are substantially impermeable to transmural blood flow, it will be obvious to those of ordinary skill in the art that the patients need not be heparinized to avoid leakage through the graft. Accordingly, it is intended by the appended claims to cover all such modifications of the invention which fall within the true spirit and scope of the invention.

What is claimed is:

1. A prosthetic vascular structure of expanded polytetrafluorethylene having:
   (i) a macroscopically tubular configuration with proximal and distal ends, and
   (ii) a microscopic superstructure of irregularly spaced nodes of various sizes and shapes interconnected by fibrils;
   said vascular structure further comprising:
   a. an average wall thickness in the range between 0.2 and 0.8 millimeters;
   b. a substantially uniform distribution of nodes throughout said tubular configuration;
   c. an average density in the range between 0.2 and 0.5 grams per milliliter; and
   d. an average distance between said nodes small enough to prevent transmural blood flow and thrombosis but no less than the maximum dimension of an average red cell;
   whereby said structure may provide for the smooth flow of blood between at least two points in a living organism while controlling cellular ingrowth through the wall of the tubular configuration to promote andnourish a thin, viable neointima over the inner surface thereof and to firmly attach said prosthetic vascular structure to adjacent tissue of said living organism.

2. The prosthetic vascular structure of claim 1 wherein said nodes are generally ellipsoidal in shape and have an average dimension along their minor axes less than three times the maximum dimension of an average red cell.

3. The prosthetic vascular structure of claim 2 wherein the major axes of said nodes are in a generally radial orientation with respect to the tubular configuration.

4. The prosthetic vascular structure of claim 1 wherein the tubular configuration thereof has an average inside diameter of less than 8 millimeters.

5. The prosthetic vascular structure of claim 4 wherein the tubular configuration thereof has an average inside diameter of between 2 and 6 millimeters.

6. The prosthetic vascular structure of claim 1 wherein the tubular configuration thereof has an average inside diameter of less than 40 millimeters.

7. The prosthetic vascular structure of claim 1 further having a tensile strength in the range between 2500 and 6500 psi.

8. The prosthetic vascular structure of claim 1 wherein the tubular configuration thereof tapers from a first inside diameter at the proximal end to a second inside diameter at the distal end.

9. The prosthetic vascular structure of claim 8 wherein said first inside diameter is in the range between 5 and 8 millimeters and the second inside diameter is in the range of between 2 and 6 millimeters.

10. A prosthetic vascular structure as set forth in claim 1 wherein said average distance between said nodes is no greater than about 80 microns.

11. The prosthetic vascular structure of claim 2 wherein the minor axes of the nodes are substantially transverse to generally radial direction of the tubular configuration.

12. A prosthetic vascular structure of expanded polytetrafluorethylene having:
   (i) a macroscopically tubular configuration with proximal and distal ends, and
   (ii) a microscopic superstructure of irregularly spaced nodes of various sizes and shapes interconnected by fibrils;
   said vascular structure including:
   a. an average inside diameter in the range between 2 and 6 millimeters;
   b. an average wall thickness in the range between 0.2 and 0.8 millimeters;
   c. a substantially uniform distribution of generally ellipsoidal nodes having major axes disposed in a generally radial orientation with respect to the tubular configuration and an average minor axis dimension less than 18 microns;
   d. an average density in the range between 0.2 and 0.8 grams per milliliter; and
   e. a tensile strength in the range of between 2500 and 6500 pounds per square inch; whereby said structure may provide for the smooth flow of blood between at least two points in a living organism while controlling cellular ingrowth through the wall of the tubular configuration to promote and nourish a thin, viable neointima over the inner surface thereof and to firmly attach said prosthetic vascular structure to adjacent tissue of said living organism.

13. A prosthetic vascular structure as defined in claim 12 wherein the distribution of nodes is such that the average internodal distance is no greater than about 80 microns.

14. A prosthetic vascular graft of expanded polytetrafluoroethylene having a microscopic structure of nodes interconnected by fibrils comprising:
   a wall thickness within the range between 0.2 and 0.8 millimeters;
   a substantially uniform distribution of nodes;
   an average density in the range between 0.2 and 0.5 grams per milliliter; and
   an average distance between nodes in the range of between about 6 to 80 microns.

15. A prosthetic vascular structure as defined in claim 14 which is in tubular form.

16. A prosthetic vascular structure as defined in claim 15 wherein the inner diameter of the graft is between 2 to 10 millimeters.

17. A prosthetic vascular structure of expanded polytetrafluoroethylene having:

(i) a macroscopically tubular configuration with proximal and distal ends, and (ii) a microscopic superstructure of irregularly spaced nodes of various sizes and shapes interconnected by fibrils;

said vascular structure including:
  a. an average inside diameter in the range between 2 and 6 millimeters;
  b. an average wall thickness in the range between 0.2 and 0.8 millimeters;
  c. a substantially uniform distribution of generally ellipsoidal nodes having minor axes disposed in a generally transverse orientation with respect to the radial direction of the tubular configuration and an average minor axis dimension less than 18 microns;
  d. an average density in the range between 0.2 and 0.5 grams per milliliter; and
  e. an average distance between said nodes small enough to prevent transmural blood flow and thrombosis but no less than the maximum dimension of an average red cell;

whereby said structure may provide for the smooth flow of blood between at least two points in a living organism while controlling cellular ingrowth through the wall of the tubular configuration to promote and nourish a thin, viable neointima over the inner surface thereof and to firmly attach said prosthetic vascular structure to adjacent tissue of said living organism.

18. A prosthetic structure as set forth in claim 17 wherein said average distance between said nodes is no greater than about 80 microns.

19. A prosthetic vascular structure as set forth in claim 17 wherein the average distance between said nodes is in the range of between 6 and 80 microns.

20. An artificial vascular prosthesis comprising expanded, porous, polytetrafluorocthylene having a microstructure consisting of nodes interconnected by fibrils which permits tissue ingrowth, wherein an average distance between nodes is not less than about 6 microns and is small enough to prevent transrmural blood flow.

21. The artificial vascular prosthesis as defined in claim 20 wherein said average—distance between nodes is not greater than about 200 microns.

22. The artificial vascular prosthesis as defined in claim 20 wherein said average distance between nodes is not greater than about 150 microns.

23. The artificial vascular prosthesis as defined in claim 20 wherein said average distance between nodes does not extend beyond 150 to 200 microns.

24. The artificial vascular prosthesis as defined in claim 20 wherein said average distance between nodes is not greater than about 80 microns.

25. A prosthetic vascular graft of expanded polytetrafluoroethylene having a microscopic structure of nodes interconnected by fibrils, said graft comprising:
  a wall thickness greater than about 0.2 millimeters and less than about 0.8 millimeters; and
  an average distance between nodes in the range of between about 6 to 80 microns.

26. A prosthetic vascular graft of expanded polytetrafluoroethylene having a microscopic structure of nodes interconnected by fibrils, said graft comprising:
  a wall thickness greater than about 0.2 millimeters and less than about 0.8 millimeters;
  an average density in the range of between about 0.2 and 0.5 grams per milliliter; and
  an average distance between nodes in the range of between about 6 to 80 microns.

27. An artificial vascular prosthesis comprising expanded, porous, polytetrafluoroetylene having a microstructure consisting of nodes interconnected by fibrils which permits tissue ingrowth, wherein an average distance between nodes is not less than about 6 microns and is not greater than about 80 microns.

* * * * *

UNITED STATES PATENT AND TRADEMARK OFFICE
CERTIFICATE OF CORRECTION

| | | |
|---|---|---|
| PATENT NO. | : 6,436,135 B1 | Page 1 of 1 |
| DATED | : August 20, 2002 | |
| INVENTOR(S) | : David Goldfarb | |

It is certified that error appears in the above-identified patent and that said Letters Patent is hereby corrected as shown below:

Column 2,
Line 19, please replace "Ln" with -- in --.

Column 3,
Line 54, please replace "transmilral" with -- transmural --.

Column 10,
Line 44, please replace ".8" with -- .5 --.

Signed and Sealed this

Eighteenth Day of March, 2003

JAMES E. ROGAN
*Director of the United States Patent and Trademark Office*

US006436135C1

(12) EX PARTE REEXAMINATION CERTIFICATE (9769th)
United States Patent
Goldfarb (10) Number: US 6,436,135 C1
(45) Certificate Issued: Jul. 26, 2013

(54) PROSTHETIC VASCULAR GRAFT (75) Inventor: David Goldfarb, Paradise Valley, AZ (US)

(73) Assignee: Bard Peripheral Vascular, Inc, Tempe, AZ (US)

Reexamination Request:
No. 90/012,716, Nov. 5, 2012

Reexamination Certificate for:
Patent No.: 6,436,135
Issued: Aug. 20, 2002
Appl. No.: 05/517,415
Filed: Oct. 24, 1974

Certificate of Correction issued Mar. 18, 2003

(51) Int. Cl.
*A61F 2/06* (2013.01)
(52) U.S. Cl.
USPC ........ 623/1.39; 623/23.71; 623/1.49; 623/1.1

(58) Field of Classification Search
None
See application file for complete search history.

(56) References Cited

To view the complete listing of prior art documents cited during the proceeding for Reexamination Control Number 90/012,716, please refer to the USPTO's public Patent Application Information Retrieval (PAIR) system under the Display References tab.

*Primary Examiner* — Beverly M. Flanagan (57) ABSTRACT

A prosthetic vascular graft with walls less than 0.8B millimeters in thickness and formed of highly expanded polytetrafluoroethylene with a microscopic superstructure of nodes and interconnecting fibrils, which nodes are substantially uniformly separated by an average distance greater than a typical red cell. The superstructure of the graft controls transmural cellular ingrowth and assures the establishment and maintenance of a thin, viable neointima.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 20-27 is confirmed.

Claims 1-19 were not reexamined.

\* \* \* \* \*